United States Patent [19]

Baran

[11] 4,241,010
[45] Dec. 23, 1980

[54] PRESSURE RESPONSIVE CONDITIONING CONTROL GAS STERILIZATION

[75] Inventor: Walter J. Baran, Erie, Pa.

[73] Assignee: American Sterilizer Company, Erie, Pa.

[21] Appl. No.: 9,818

[22] Filed: Feb. 6, 1979

[51] Int. Cl.$^3$ ............................ A61L 2/20; A61L 2/24
[52] U.S. Cl. ........................................ 422/2; 422/27;
422/28; 422/33; 422/34; 422/112; 422/114;
422/117; 422/295
[58] Field of Search ...................... 422/34, 27, 2, 3, 33,
422/37, 28, 26, 112, 114, 116, 117, 295, 300

[56] References Cited

U.S. PATENT DOCUMENTS

| | | | |
|---|---|---|---|
| 2,080,179 | 5/1937 | Merriam et al. | 422/27 |
| 2,131,134 | 9/1938 | Baer et al. | 422/31 |
| 2,188,371 | 1/1940 | Merriam | 131/133 |
| 3,035,886 | 5/1962 | Hickey | 422/27 |
| 3,068,064 | 12/1962 | McDonald | 422/34 |
| 3,206,275 | 9/1965 | Sair et al. | 422/33 |
| 3,409,389 | 11/1968 | Bjork | 422/26 |
| 3,436,170 | 4/1969 | Lodge | 422/26 |
| 3,494,725 | 2/1970 | Irons et al. | 422/26 |
| 3,598,516 | 8/1971 | Shull et al. | 422/27 |
| 3,795,483 | 3/1974 | Grafingholt | 422/26 X |
| 3,861,875 | 1/1975 | Joslyn | 422/111 X |
| 3,910,761 | 10/1975 | Hopkins | 422/108 |
| 3,954,406 | 5/1976 | Chamberlain | 422/27 |
| 4,164,538 | 8/1979 | Young et al. | 422/26 |

FOREIGN PATENT DOCUMENTS 3137 of 1903 United Kingdom .
488638 7/1938 United Kingdom .
542554 1/1942 United Kingdom .

OTHER PUBLICATIONS

S. S. Block; "Disinfection, Sterlization and Preservation"; publ. by Lee & Febger; Phila. Pa.; 1977; pp. 493-508.
J. J. Perkins; "Principles & Methods of Sterlization in Health Sciences"; publ. by C. C. Thomas; Springville, Ill.; pp. 110-114; 150-152 & 501-530.
"Developments in Industrial Microbiology"; vol. 18; Society for Industrial Microbiology; pp. 335-351.

Primary Examiner—Barry S. Richman
Attorney, Agent, or Firm—Shanley, O'Neil and Baker

[57] ABSTRACT

Biocidal gas sterilization methods and apparatus are disclosed in which goods are heated and moisturized prior to addition of the sterilizing gas utilizing repressurization after initial evacuation to provide drive power for the conditioning vapor and improve conditioning efficiency. After initial evacuation to a selected subatmospheric pressure level, the chamber is repressurized with a conditioning vapor comprising steam to a subatmospheric pressure level corresponding approximately to desired sterilizing temperature, then the chamber is held with evacuating and vapor injecting interrupted for a predetermined interval; this sequence of steps is repeated a selected number of times; and, conditioning to various sterilizing temperatures is available. Initial evacuation can be accompanied by intermittent injection of conditioning vapor. No chamber measurement of temperature or relative humidity is required for conditioning control and conditioning vapor injection is free of flow rate control requirements.

10 Claims, 4 Drawing Figures

PRESSURE RESPONSIVE CONDITIONING CONTROL GAS STERILIZATION

This invention is concerned with gas sterilization and, more particularly, with improved conditioning of goods for biocidal gas sterilization.

In conditioning goods for ethylene oxide sterilization, desired temperature and moisture conditions should be achieved throughout the goods to be sterilized. In the past, this has required extended time periods, or provision of conditioning materials and energy often substantially in excess of that needed for heating and moisturizing the load, or instrumentation which required operator steps or instruments which may not remain reliable under sterilizing conditions.

In the prior practice, often referred to as the static method of conditioning, moisture is added and held in an otherwise sealed chamber while the goods are heated by the chamber walls. This approach can take extended periods of time, especially with soft goods loads, for conditions to exist in the load for an optimum kill rate of microorganisms; therefore, extended sterilization cycle times result.

In other prior practice, described as dynamic conditioning, steam flows through the chamber while the chamber is being evacuated. Heating and moisturizing of the goods are expedited and total sterilization cycle times are thereby shortened; but, larger amounts of moisture and heat are pumped from the chamber during the conditioning phase; also, checks on conditioning operation have not been readily available, selection of conditioning values is minimal, and the opportunities for developing wet packs with certain types of loads are greater than desired.

More recently, conditioning approaches have been suggested in which temperature and humidity sensors are imbedded in the goods to be sterilized for the purpose of signaling conditions within the goods; such approaches can have inherent disadvantages in the accuracy and functioning of sensors and requires placement of the sensors by the operator before start of the cycle. In any of the prior art, the imposition of conditioning steam flow rate requirements can cause difficulties in achieving proper control and in maintenance and service requirements.

Such shortcomings of the prior art are substantially reduced or eliminated by practicable minimizing of conditioning vapor, instrumentation, and flow rate control requirements while providing effective and efficient conditioning of the goods to be sterilized.

The invention eliminates any requirement for humidity sensing equipment or temperature sensing equipment in the load, or in the sterilizing chamber, for purposes of control of conditioning. In addition, a cycle is provided in which conditioning vapor injection is independent of rate control requirements so that prior art requirements for needle valves or other flow rate control devices of conditioning steam can be eliminated.

Further, a conditioning drive power, which increases load conditioning efficiency, is provided by controllably changing chamber pressures to facilitate early attainment and control of moisture and heat requirements within the load. In comparison to the flow-through teachings of the prior art, conditioning material and energy are conserved with most loads and the likelihood of wet packs substantially reduced or eliminated. Also, total sterilization cycle times are considerably shortened over those available with static methods of the prior art and do not exceed those available with the prior flow-through methods. And, verification of actual conditioning, while in process, is readily available.

Optimum kill-rate temperature and humidity conditions are established in the load prior to addition of the biocidal gas. The desired load temperature established during conditioning and gas charge can be readily maintained in the chamber during the sterilizing phase. The moisture requirements for sterilization established during conditioning are held within the chamber during sterilization. Conditioning prior to adding biocidal gas enables sterilization to take place in shorter time periods utilizing generally accepted ethylene oxide concentrations of about 600 to 700 mg. of ethylene oxide (ETO) per liter of sterilizing chamber volume at pressures from about five (5) to ten (10) psig of a mixture of 12% ETO and 88% diluent gas.

With conditioning and ethylene oxide concentrations established, sterilization times are dependent on the temperature selected for the cycle. The present invention can provide for sterilization cycles at differing temperatures within the range accepted as practical, generally above 100° F. to about 160° F. (above about 40° C. to about 75° C.) for so-called "cold" sterilization; and, additionally, the inventive system can provide for a variety of sterilizing chamber sizes and chamber loads.

In addition to initial evacuation, the conditioning phase includes a plurality of repressurizations accomplished by injection of a conditioning vapor (typically steam) having heat transfer and moisturizing properties. Initial evacuation to a subatmospheric pressure level, below that corresponding to the desired sterilization temperature, is followed by repressurization to a higher subatmospheric pressure level corresponding to the pressure level for the vapor which establishes approximately the desired sterilization temperature. Such repressurizations at subatmospheric pressure levels provide a drive power for the conditioning vapor which enhances penetration of heat and moisture into the load. Between repressurizations, chamber evacuating and steam injecting are interrupted for predetermined intervals.

The goods to be sterilized are heated and moisturized by the conditioning steps and, chamber walls are preferably held at desired sterilization temperature during the sterilizing phase to avoid heat losses from the vicinity of the load.

Advantages and contributions of the invention are considered in more detail in describing the invention in relation to the accompanying drawings.

Figure 1:
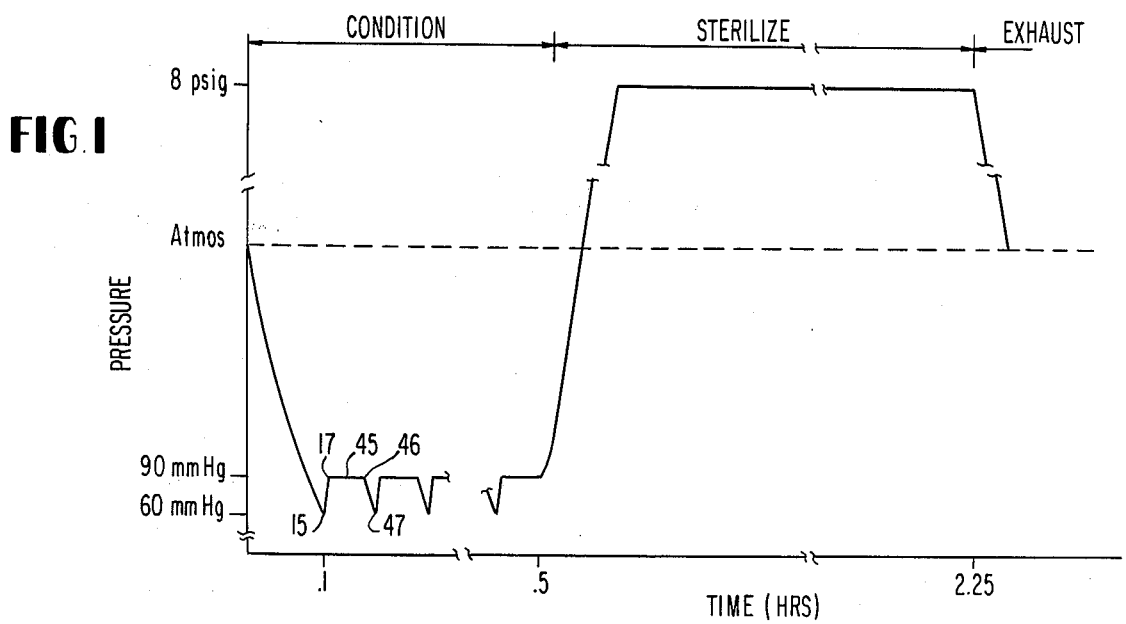
FIG. 1 is a pressure vs. time graph representation of a cycle including conditioning, sterilizing, and exhaust phases for carrying out the invention.

For purposes of a detailed description, an embodiment of the invention carried out at about 130° F. (54° C.), a temperature widely used for sterilizing various loads including hard goods, fabrics, and plastics, is presented. As shown in FIG. 2, a pressure vessel 10 is connected to vacuum source 12 for evacuation to desired subatmospheric pressures. As indicated at point 15 in FIG. 1, the chamber is initially evacuated to a subatmospheric pressure level of about 60 mm. Hg.

A conditioning vapor capable of transferring latent heat through condensation, such as steam, is fed from source 20 through conduit 22 to the chamber under the control of on/off valve 24. Injection of this vapor raises the pressure to a second selected higher subatmospheric pressure of 90 mm. as indicated by point 17 in FIG. 1; this pressure corresponds approximately to the temperature desired for sterilization as determined by the interrelationship of pressure and temperature available from steam or other vapor tables.

A significant contribution of the invention is provision for the conditioning vapor used to be injected without requiring injection rate control of the vapor additions; for example, steam can be used at available pressures, typically from about 50 to 80 psig, without requiring needle valve or other flow rate controls, thus eliminating possibly troublesome devices.

In the 130° F. cycle, chamber pressure is reduced during the initial evacuation to the lower of two selected subatmospheric pressures, about 60 mm. Hg., then raised to the subsequent higher subatmospheric pressure of about 90 mm. Hg. The second higher subatmospheric pressure selected should provide a temperature around 125° thus allowing for the heat of pressurization produced by adding biocidal gas above atmospheric pressure after conditioning and, compensating partially for the higher temperature which can occur within dry fabric packs when moisturizing and heating by condensation of the conditioning vapor.

The evacuation and repressurization levels for conditioning can be preset on pressure switch means to provide pressure responsive on/off control of vacuum and steam injection. Sensing of temperature or relative humidity are not required for control of conditioning process steps.

Chamber pressure determinations can be made with pressure sensor 28 which sends a pressure signal through electrical connector 30 to control 32 which, in turn, sends a control signal over electrical connector 34 to solenoid 36 for on/off control of valve 24 in steam line 22.

Control 32 also actuates on/off valve 38 in vacuum line 40 through signal connector 42 interconnecting control 32 to valve operating solenoid 44. Vacuum source 12 can be a vacuum pump of the type and size standardly accepted as economically and operationally practical for the particular size chamber.

Evacuation is interrupted at 60 mm. Hg. (point 15 of FIG. 1) and steam is injected. As the 90 mm. Hg. pressure is reached (at point 17 in FIG. 1), steam injection is interrupted. With both steam injection and evacuation interrupted, the chamber is held in this sealed condition for a predetermined interval; for example, three minutes, as indicated by line 45 of FIG. 1.

At the end of this predetermined time (point 46) during which the chamber is sealed, control 32 opens vacuum valve 38 to evacuate the chamber to approximately the initial subatmospheric pressure, about 60 mm. Hg. as indicated by point 47 in FIG. 1. To facilitate handling mixed loads, a pressure differential of 30 mm. of Hg. is selected but a lower pressure increment can be satisfactory under certain load conditions.

The sequence of evacuating to about 60 mm. Hg., repressurizing to about 90 mm. Hg., and then holding the chamber without evacuating or injecting steam for a predetermined interval is repeated. The number of these repeated sequences is preselected to provide desired conditioning prior to the sterilization phase; for example, in a 130° F. cycle, with a vacuum pump rated at about twenty-five cfm used on a sterilizer from above fifteen to about thirty cubic feet, repressurization is set to occur five times; with a vacuum pump rated at about two and a half cfm used on a sterilizer chamber between about seven and a half to about ten cubic feet, repressurization is set to occur three times to accomplish desired conditioning of all types of loads.

All packs in multiple pack loads are conditioned for temperature and humidity prior to admission of the biocidal gas. Mixed full loads included cardboard box packs, obstetrics packs, Canadian Standards Association packs, a Federal specification pack, an Emergency Caesarian pack, paper/plastic peel pouches, and a plastic bedpan subpack. Biocidal gas (12% ETO, 88% diluent gas) held at a pressure of eight (8) psig to provide approximately 650 mm. per liter of ETO concentration provides 100% kill of Bacillus subtilii (globigii) with an exposure time of one and three-quarters (1¾) hours which includes an adequate safety factor assuring sterilization for hospital practice. With such mixed full loads, and with single pack loads, all packs were heated to approximately desired sterilization temperature and humidified during the conditioning phase to approximately 60% to 100% RH.

Figure 3:
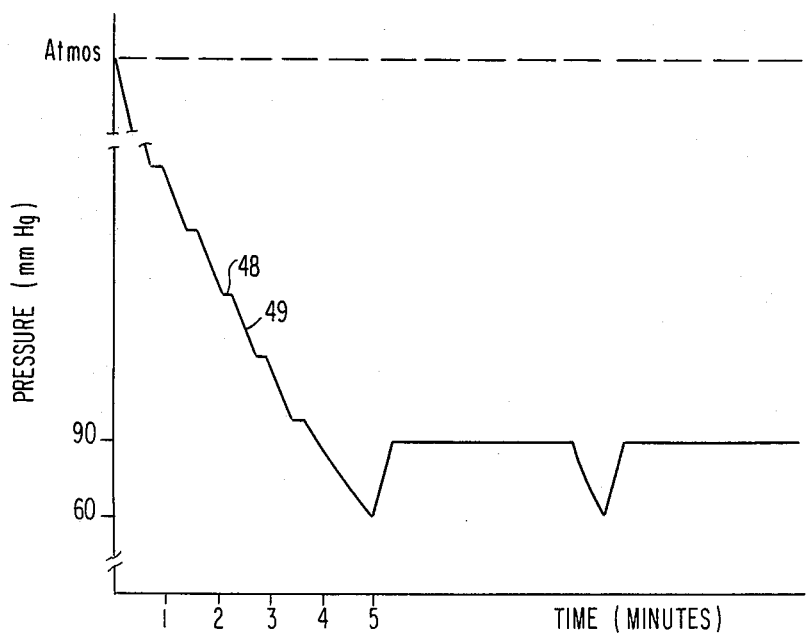
FIG. 3 is an enlarged view of a portion of FIG. 1 showing a specific embodiment of an initial evacuation phase.

In the embodiment of FIG. 3, the steam valve 24 is opened intermittently during initial evacuation. In a typical pulsing arrangement, steam is added in five (5) second pulses (indicated by reference numeral 48 in FIG. 3) at thirty (30) second intervals (indicated by reference numeral 49). This steam purge arrangement helps provide for more rapid load conditioning to temperature. Evacuation continues during the short steam injection purge pulses; in the later vapor injection phases, evacuating is terminated to reduce heat and energy losses.

The short pulse injection method enables use of a vapor injection purge which contributes the versatility of the cycle. Use of vapor injection during initial evacuation to facilitate heat-up is especially suited to cycles in the upper portion of the commercial practical ethylene oxide sterilization temperature range, i.e. about 125° F. and higher. Selecting a short injection pulse followed by a substantially longer interval without steam injection enables use of on/off steam injection free of rate control over a wide range of steam pressures. Load heating efficiency is increased while avoiding overheating of the load. The ratio of injection pulse time to interval time between pulses can about 1:5; in the 130° F. cycle with steam injection pulses taking place during the initial evacuation to 90 mm. Hg., a ratio of 1:6 provides satisfactory results.

With cycles at the lower end of the accepted practical temperature range for ethylene sterilization, e.g. above 100° F. to less than 125° F., steam purge pulses would generally not be utilized because it would not be practical to provide the evacuating capacity needed to avoid overheating items which might be sterilized at such low temperatures. As the desired cyclic temperature increases, the steam pulsing purge can be limited to later portions of the initial evacuation when injected steam temperature more closely approaches desired sterilization temperature. The vapor injection purge pulses generally terminate during the initial evacuation as the 90 mm. Hg. pressure level is reached.

The on/off valve 24 is the only valve required in the conditioning steam line 20 for flow purposes (a check valve can be used for other purposes). Major advantages of the present vapor injection teachings include elimination of needle valves on conditioning steam lines; this eliminates needle valve clogging problems and needle valve adjustment problems in usage. Not only is this potential problem area eliminated but on/off steam flow facilitates rapid verification that conditioning vapor is being injected.

With the pressure responsive teachings of the invention, verification of conditioning can be readily obtained since conditioning vapor injection is required to establish pressure relationships in the chamber which are utilized in determining whether the cycle is to proceed. Subatmospheric repressurization times longer than a fraction of a minute, which are readily discernible, provide a check that conditioning is proceeding. The concept of conditioning verification was not available in prior practice. With the present teachings, parameters on chamber pressure vs. lapsed time can be used to indicate when conditioning is not proceeding and to abort the cycle.

Apparatus requirements are also reduced in the control portion of the present system. Timer sequencing means are utilized; however, pressure levels are the only chamber sensed determinations required for operation of conditioning steps. While chamber wall temperature can be thermostatically controlled, as in prior practice, chamber temperature sensors or relative humidity sensors are not required for the conditioning steps to proceed reliably. Also, the same steam line and variable steam pressures can be used for various temperature cycles; the present system can be effective at substantially lower steam pressures than generally available; however, cycle efficiency is better maintained at steam pressures of 35 psig and higher.

Basically, control 32 includes elements to receive incoming pressure signals and, through timer and sequencing means, coordinates on/off valve operations and times. After chamber 10 is loaded with goods to be sterilized, closure 50 seals the chamber for operation at pressures other than atmospheric. After completion of the conditioning phase, as described, the chamber is charged with a biocidal gas from source 51 under control of valve 52 which is actuated by solenoid 53.

Pressure sensing means can be divided for practical purposes, i.e. to provide accuracy with economy, into a pressure switch operable at the subatmospheric levels of sixty (60) and ninety (90) mm. and a pressure switch operable at supra-atmospheric pressures of about ten (10) psig as used for the biocidal gas. To minimize heat losses during the sterilization phase, the sterilizer chamber walls can be maintained at about 130° F. through thermostat 54 by electrical strip heaters or by a steam jacket.

Solenoid-operated valves, pressure sensors, timer and sequencing means, and steam, gas, and vacuum sources described above are commercially available and need no further description. A novel combination of these individually known elements effects conditioning control while eliminating the need for load contact sensors, chamber relative humidity gages, and needle valve type flow control of steam injection.

The various chamber evacuation and injection means are controlled relying ultimately only on sensing chamber pressure and time measurements which provide for continuing reliability. Initial evacuation is pressure responsive and purge vapor injection pulses are timer controlled. Pulse evacuation and repressurization phases are pressure responsive and intermediate intervals are timer controlled. Charging biocidal gas and sterilizing gas pressure are pressure responsive. Measured pressures and time intervals can be combined by electromechanical or other electrical control elements in the light of the present teachings.

Figure 4:
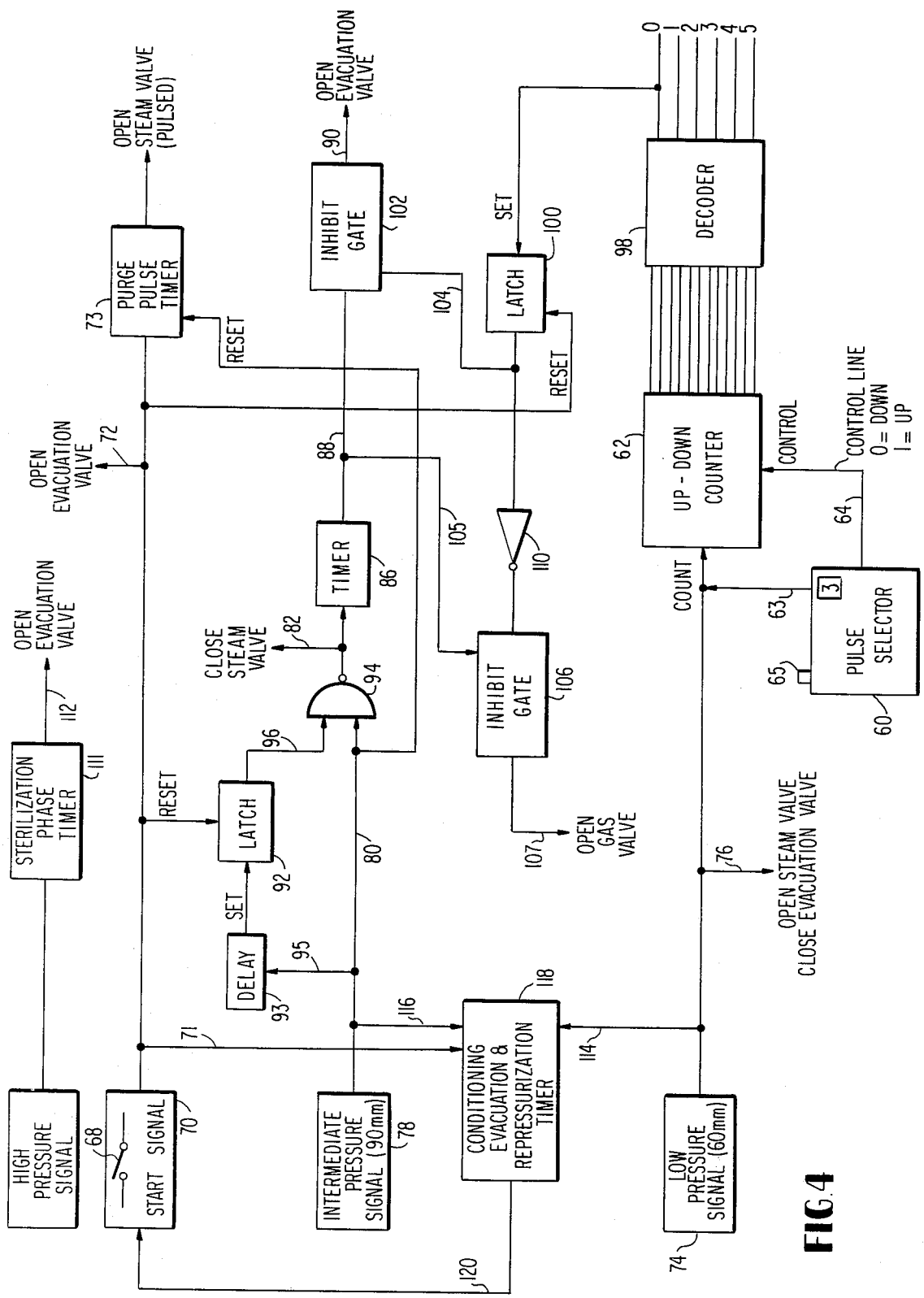
FIG. 4 is a schematic circuit diagram of a control apparatus embodiment of the invention.

In the electronic control arrangement of FIG. 4, the number of repressurization sequences can be preset and fixed before the process is begun for a particular sterilizer or selected by operating or service personnel. The desired number of repressurization pulse sequences is selected at pulse selector 60 which loads up-down counter 62 accordingly. A pulse is generated on both output lines 63, 64 by the pulse selector circuit each time button 65 is depressed. The counter can be operated in two modes and is arranged so that, when its control input is a zero (low or no signal), the counter counts down and, when its input is a "one" (high signal), the counter counts up. Since control line 64 will be a "one" (high signal) each time a pulse is fed from pulse selector 60 to the count input of up-down counter 62, the counter will up count to a number corresponding to the number of repressurization sequences selected at button 65.

With the up-down counter 62 preloaded, the cycle is started by closing switch 68 of start signal generator 70. This generates an electrical signal on line 72 which opens the evacuation valve 38 of FIG. 2 through solenoid valve 44.

Initial evacuation is continuous to a preselected subatmospheric level and can include a series of short time interval steam pulses as shown in the graph of FIG. 3. When the vapor injection purge is used, steam pulse timer 73 provides pulsed operation of solenoid 36 to open and close steam valve 24 of FIG. 2 during initial evacuation between atmospheric pressure and 90 mm. Hg. as shown in FIG. 3 and previously described. Pulse timer 73 is reset from intermediate signal generator 78 over line 80 to be operative only during the initial evacuation.

In the 130° F. cycle described, evacuation continues after the initial purge evacuation until the pressure in the chamber reaches 60 mm., whereupon low pressure signal unit 74 generates an output signal. This output signal on line 76 is effective to close the evacuation valve 38 and open the steam valve 24. Steam injection causes the pressure in the chamber to rise to 90 mm. (point 17 in the graph of FIG. 1). When the chamber pressure reaches 90 mm., intermediate pressure signal generator 78 generates an output signal on line 80 which is effective, via line 82, to close the steam valve 24 and, via line 84, to activate timer 86.

After the three-minute delay during which both steam injection and evacuation are interrupted, a signal from timer 86 on line 88 is effective to open the evacuation valve again by a signal on line 90. When the pressure is reduced to 60 mm. again, the evacuation valve 38 is closed and the steam valve 24 is opened; and, sequencing as described above continues until the conditioning phase is ended by completion of the preselected number of sequences.

Additional means are provided to prevent intermediate pressure signal unit 78 from generating a signal when the ninety (90) mm. pressure level is first reached during the initial evacuation. This may be effected by providing latch 92, delay means 93, and AND gate 94.

The first time that the pressure falls to the intermediate pressure level (90 mm.) and intermediate pressure signal unit 78 generates a signal, such signal is fed on line 80 to a first input terminal of AND gate 94 and, simultaneously, is fed on line 95 to delay network 93 which is set to delay the signal by a fraction of a sequence. After the signal is delayed, it is fed to the set input of latch 92 thereby setting the latch. The output of the latch 92 is fed on line 96 to the second input terminal of AND gate 94. However, due to the delay, it does not arrive at the AND gate until after the first output signal of intermediate pressure signal unit 78 has disappeared from the first input to the AND gate. Therefore, the first output signal does not pass through the AND gate and is not effective to close the steam valve or to set the timer 86. However, since the latch 92 remains set for all subsequent sequences in the conditioning phase, all output signals of intermediate pressure signal unit 78 after the first signal pass through AND gate 94 are effective to close the steam valve and to set the timer 86 to carry out the prescribed pulsing sequence.

After the last sequence in the conditioning phase, biocidal gas is added to raise chamber pressure to a selected supra-atmospheric pressure level such as eight (8) psig. The last conditioning sequence is detected by up-down counter 62 and decoder 98. When the counter counts down to zero, the decoder output will become high. This signal is fed to the set input terminal of latch 100, the output of which is fed to INHIBIT gate 102 on line 104. INHIBIT gate 102 is effective to pass the output signal of timer 86 at all times except when the latch 100 input to the INHIBIT gate is high. Thus, after the pressure reaches 90 mm. in the last sequence, the output of the timer 86 is prevented by INHIBIT gate 102 from being fed through to the circuit point for opening the evacuation valve. Instead, the output of the timer 86 is effective to open the gas valve 52 (FIG. 2). As shown in FIG. 4, this output is fed via line 105 through INHIBIT gate 106 to line 107 for opening the gas valve 52. This signal is inhibited by the output of latch 100 and inverter 110 at all times except after the last sequence when latch 100 becomes set. Both of the latches 92 and 100 are reset by the start signal generator 70 at the beginning of a conditioning phase; the start signal generator 70 can also reset the up-down counter 62 to "start" condition.

Figure 2:
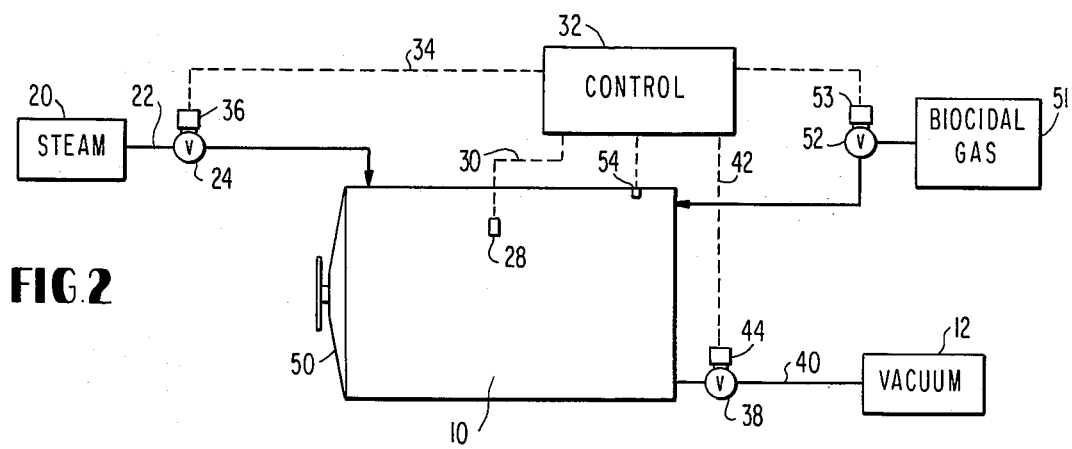
FIG. 2 is a schematic diagram of apparatus embodying the invention.

The entry of biocidal gas is continued until the chamber pressure reaches about eight (8) psig, whereupon high pressure signal unit 108 generates a signal which is effective to close the gas valve 52 through solenoid 53 (FIG. 2) and, after a time delay equal to the sterilization phase time introduced by timer 111, is also effective to open the evacuation valve 38 by a signal on line 112; this completes the sterilization phase as depicted in FIG. 1.

Means are provided to abort the cycle when transition times between the two selected subatmospheric levels exceed reasonable preset parameters. Considering a hospital sterilizer having a chamber volume of about twenty-five cubic feet, mixed full pack, 130° F. cycle, initial vacuum to 90 torr (with five second steam pulses at thirty second intervals) takes approximately 4 to 4.5 minutes, evacuation from 90 to 60 torr about one minute, repressurization to 90 torr about ½ to ¾ minute, chamber hold three minutes, evacuate to 60 torr about 1 minute, repressurization to 90 torr about ½ to ¾ minute, etc. through five repressurizations. Gas charge to eight (8) psig can take from about 7.5 to 15 minutes. Sterilization time, with safety factor, is arbitrarily set at 1¾ hours. Exhausting and air breaks, after sterilization, can take from 10 to 15 minutes. The total cycle time for 130° F. sterilization temperature is about 2¾ hours.

In order to verify that initial evacuation and conditioning are proceeding, any of the allowable preset parameters can be checked through evacuation and conditioning timer 118. Transition times, e.g. any of the repressurization times between 60 and 90 mm. Hg., such as between points 15 and 17 of FIG. 1, during the sequencing, can be evaluated. The repressurization phase, with on/off control of steam should be less than one minute in hospital sterilizers. The time between the low pressure signal from the low pressure signal generator 74 on line 114 and the intermediate pressure signal for the intermediate pressure signal generator 78 delivered on line 116 are compared in timer 118. Excessive repressurization times cause a signal to be generated on line 120 which interrupts the cycle through start signal generator 70.

Criteria met by these teachings include sterilization efficiency with various types of loads enabling mixing of load materials (hard good, fabrics, rubber and plastic material, and instruments), avoidance of wet packs or damaged loads, and compliance with governmental test specifications (Fed Spec GG-S-1344A-Nov. 26, 1975). Content data for the Canadian Standards and Federal Specification Packs are published; in addition, the mixed full loads tested included two cardboard filled boxes weighing approximately fifteen pounds apiece, two boxes of OB pads weighing approximately ten pounds each, two wrapped plastic bedpans, an emergency Caesarian pack, and paper/plastic pouches containing surgical or anesthesia equipment. Conditioning to desired moisture and temperatures was verified in packs, previously considered difficult to heat, with five sequences for such mixed full load.

Biological spore strips, tested to assure a minimum average population per strip of $1 \times 10^6$ spores of Bacillus subtilis (globigii), were used with 100% kill of microorganisms consistently obtained. At 130° F., a 1¾ hour gas exposure period provides adequate safety factor to meet hospital specifications. With baffling to prevent direct impingement of incoming steam onto the load, wet packs are avoided and load conditioning is consistently completed before gas charge. The sterilization phase times can be decreased at higher temperatures and increased at lower temperatures in accordance with established skills in gas sterilization.

In disclosing the principles of the invention, specific embodiments, cycle values, and apparatus have been described. With such teachings, modifications can be made and apparatus substituted, other than as specifically described, by those skilled in the art while relying on the principles of the invention. Therefore, the scope of the invention should be determined with reference to the appended claims.

I claim:

1. Method for conditioning goods for sterilization and sterilizing goods with a chemically biocidal gas in a sealable chamber capable of operating at pressures other than atmospheric, the conditioning including heating the goods to a selected temperature related to the desired sterilization temperature and moistening the goods to a desired level for such biocidal gas sterilization, with conditioning steps being free of temperature and moisture measurement requirements in the goods and in the chamber, comprising the steps, after closing the chamber to permit operation at pressures other than atmospheric, of evacuating the chamber to a preselected subatmospheric level, supplying a condensable conditioning vapor having heating and moisturizing properties for heating and moisturizing goods to be sterilized, such vapor having a determinable interrelationship between pressure level and temperature, injecting such conditioning vapor into the chamber to raise chamber pressure to a second preselected subatmospheric pressure level corresponding to approximately desired sterilization temperature based on the interrelationship of pressure level and temperature of the condensable conditioning vapor, such injecting of conditioning vapor being free of flow rate adjustment control requirements, then holding the chamber in sealed condition for a predetermined time with evacuating and vapor injecting interrupted, then repeating such sequence, of evacuating the chamber followed by injecting conditioning vapor to repressurize the chamber to the preselected subatmospheric pressure corresponding to approximately desired sterilizing temperature and holding the chamber in sealed condition for a predetermined time with evacuating and vapor injecting interrupted, a preselected number of times to establish desired temperature and moisture conditions in goods to be sterilized, then adding chemically biocidal gas while the chamber is otherwise sealed to raise chamber pressure to a desired supraatmospheric pressure, and holding such biocidal gas in the chamber for a time period to complete desired sterilization.

2. The method of claim 1 in which such sequence, including evacuating to a predetermined subatmospheric pressure level, injecting conditioning vapor to raise chamber pressure to a pressure level corresponding approximately to that of desired sterilization temperature, and holding the chamber with evacuating and vapor injecting interrupted, is carried out at least three times.

3. The method of claim 1 in which the temperature of the goods to be sterilized is maintained by maintaining a chamber wall portion at approximately desired sterilization temperature while the chemically biocidal gas is in the chamber.

4. The method of claim 1 including
establishing a preselected time limit for repressurizing the chamber between such two preselected subatmospheric pressure levels which is indicative of proper system operation during the conditioning phase, and
interrupting the conditioning and sterilizing cycle when repressurizing time during a sequence exceeds such preselected time limit.

5. The method of claim 1 in which the condensable conditioning vapor comprises steam and the chamber is evacuated initially to a subatmospheric pressure in the range of about 50–70 mm. Hg.

6. The method of claim 5 in which the increment of pressure increase achieved by injecting steam to raise chamber pressure to the preselected subatmospheric pressure level corresponding to desired sterilization temperature is in the range of about 15–30 mm. Hg.

7. The method of claim 1 including the further step of adding the condensable conditioning vapor during a portion of such initial evacuation to a preselected subatmospheric pressure level.

8. The method of claim 7 in which the conditioning vapor is added during such initial evacuation by intermittently injecting the conditioning vapor to provide a plurality of short vapor injection pulses as the chamber is being evacuated.

9. The method of claim 8 in which
said intermittent injections are free of flow rate adjustment control during injecting of such conditioning vapor, and
the ratio of the time duration of the vapor injection pulses to the time interval between such injection pulses during such chamber initial evacuation phase is selected to avoid overheating the goods substantially above desired sterilization temperature.

10. Method for conditioning and sterilizing goods with a chemically biocidal gas in a sealable chamber capable of operating at pressures other than atmospheric, the conditioning including heating the goods to a selected temperature related to the desired sterilization temperature and moistening the goods to a desired level for such biocidal gas sterilization with conditioning steps being responsive to chamber pressure and independent of temperature and relative humidity measurement requirements, comprising the steps of
loading goods to be sterilized into the chamber and closing the chamber to permit operation at pressures other than atmospheric,
supplying steam at a pressure of about 35 to 80 psig,
evacuating the chamber to about 90 mm. Hg. while intermittently injecting steam in pulses of about five second duration spaced by selected time intervals of about thirty second duration,
interrupting such intermittent steam injection while continuing such chamber evacuating to about 60 mm. Hg., then
injecting steam to raise the pressure within the chamber to about 90 mm. Hg.,
such steam injection into the chamber and such earlier intermittent pulse steam injections being free of injection flow rate adjustment requirements, then
holding the chamber in sealed condition for about three minutes with evacuating and steam injecting interrupted, then
repeating such sequence of evacuating to about 60 mm. Hg., repressurizing to about 90 mm. Hg., and holding the chamber in sealed condition for about three minutes with evacuating and vapor injecting interrupted to heat and moisturize the goods to desired levels, then
adding ethylene oxide and a diluent gas to raise chamber pressure above atmospheric pressure while maintaining the chamber in otherwise sealed condition,
maintaining a wall portion of the chamber at approximately desired sterilization temperature to minimize heat losses from the load, then
holding the ethylene oxide, diluent gas, and conditioning moisture at a pressure above atmospheric pressure in the sealed chamber to complete desired sterilization, and, then
removing such gases from the chamber to return the chamber to atmospheric pressure for removal of the sterilized goods.

\* \* \* \* \*